United States Patent
Freese et al.

(10) Patent No.: US 7,953,788 B2
(45) Date of Patent: May 31, 2011

(54) SYSTEM AND METHOD FOR QUEUING DATA FOR AN APPLICATION SERVER

(75) Inventors: Agnes Freese, Niwot, CO (US); Jeffrey Fischer, San Francisco, CA (US); Peter Siam Sy Lim, III, Redwood City, CA (US)

(73) Assignee: Siebel Systems, Inc., San Mateo, CA (US)

( * ) Notice: Subject to any disclaimer, the term of this patent is extended or adjusted under 35 U.S.C. 154(b) by 1698 days.

(21) Appl. No.: 09/968,134

(22) Filed: Sep. 29, 2001

(65) Prior Publication Data
US 2007/0250600 A1 Oct. 25, 2007

(51) Int. Cl.
*G06F 15/16* (2006.01)
(52) U.S. Cl. ........ 709/202; 709/203; 709/219; 707/607; 719/314; 719/330
(58) Field of Classification Search .................. 709/219, 709/201–203; 707/4, 102, 202
See application file for complete search history.

(56) References Cited

U.S. PATENT DOCUMENTS

| | | | | |
|---|---|---|---|---|
| 4,949,251 A * | 8/1990 | Griffin et al. | ................... | 714/20 |
| 5,151,978 A * | 9/1992 | Bronikowski et al. | ........ | 709/216 |
| 5,559,957 A * | 9/1996 | Balk | ................................ | 714/23 |
| 5,794,234 A * | 8/1998 | Church et al. | ................... | 707/4 |
| 5,812,768 A * | 9/1998 | Page et al. | ..................... | 709/228 |
| 6,148,305 A * | 11/2000 | Ikegaya et al. | ............. | 707/104.1 |
| 6,199,068 B1 * | 3/2001 | Carpenter | ..................... | 707/100 |
| 6,256,676 B1 * | 7/2001 | Taylor et al. | ................... | 709/246 |
| 6,516,423 B1 * | 2/2003 | Stenlund et al. | ................... | 714/4 |
| 6,549,936 B1 * | 4/2003 | Hirabayashi | .................. | 709/205 |
| 6,662,213 B1 * | 12/2003 | Xie et al. | ....................... | 709/206 |
| 6,711,607 B1 * | 3/2004 | Goyal | ........................... | 709/203 |
| 6,721,747 B2 * | 4/2004 | Lipkin | ........................... | 707/10 |
| 6,738,975 B1 * | 5/2004 | Yee et al. | ....................... | 719/310 |
| 6,775,680 B2 * | 8/2004 | Ehrman et al. | ................. | 707/102 |
| 2001/0047348 A1 * | 11/2001 | Davis | ................................. | 707/1 |
| 2003/0163585 A1 * | 8/2003 | Elderon et al. | ................ | 709/246 |

* cited by examiner

*Primary Examiner* — Andrew Caldwell
*Assistant Examiner* — Christopher D Biagini
(74) *Attorney, Agent, or Firm* — Campbell Stephenson LLP (57) ABSTRACT

A method for queuing data for an application server is described. The method includes creating a queue entry record corresponding to the data, storing a queue entry including the data and the corresponding queue entry record in a queue, and receiving a command regarding the data from the application server.

27 Claims, 9 Drawing Sheets

SYSTEM AND METHOD FOR QUEUING DATA FOR AN APPLICATION SERVER

BACKGROUND

Many businesses are continually searching for new ways to respond more rapidly to their customers' needs. Decision-makers require immediate access to accurate information to make immediate changes to business processes. Enterprise application integration (EAI) addresses these needs by enabling multiple applications within an organization to share information and functionality to automate business processes.

EAI provides the ability to integrate islands of automation without replacing existing legacy systems that perform satisfactorily. To accomplish this, an EAI architecture incorporates application-to-application adapters, business rules, data transformation technologies, and workflow management. For example, an EAI architecture can include interfaces to various databases and integrated business application programs.

One example of such databases and integrated business application programs is SAP R/3, which is a set of databases and integrated business application programs from Systems, Application and Products in Data Processing from SAP AG of Germany. SAP R/3 uses a client-server model and provides the ability to store, retrieve, analyze, and process corporate data for financial analysis, production operation, human resource management, and other business processes. SAP R/3 includes features designed to speed product delivery by helping to manage the supply chain. SAP R/3 can access the SAP R/3 database and applications through the Internet using a Web browser. For example, a sales representative can initiate the workflow for a sales order by filling out an electronic form on a laptop that is "translated" into input for the SAP R/3 system. Other interfaces such as Lotus Notes can also be used. The Web implementation adheres to the Workflow Client API standard of the Workflow Management Coalition (WfMC).

An example of such a workflow management (WFM) system is SAP Business Workflow from SAP AG, which is a database-centered WFM system that uses R/3 to provide an enterprise with standard functionality for information processing. It will be noted that SAP Business Workflow is integrated into R/3 and is not a stand-alone system. Such systems typically employ a standard document format Intermediate Document (IDOC) is one such standard SAP document format. IDOCs allow different application systems to be linked via a message-based interface. One goal of the IDOCs standard is to allow business documents to be exchanged and processed automatically. The various degrees of structural complexity in different application systems can be reduced to a structure which is as simple as possible. Additionally, IDOC allows for extensive exception handling before the data is posted to the application.

Business application program interfaces (BAPIs) are programming interfaces to access the SAP Database from within SAP or other development platforms external to R/3 that support the Remote Function Call (RFC) protocol. The main objective of BAPI is to achieve integration between the R/3 System and external applications, legacy systems, and the like. BAPIs are defined in the Business Object Repository (BOR) as methods of SAP Business Objects or SAP Interface Types and enable object-oriented access to Business Components (application components) in the R/3 System. BAPIs can be accessed from various programming environments, for example, Java, C++, Visual Basic. Web based access to the SAP database is also supported. Several standard terms are now explained, to allow for a full and accurate discussion of the functionalities of such systems:

1) The term ABAP is a programming language used with SAP.
2) The term Remote Function Call (RFC) refers to SAP technology that allows external applications to call ABAP functions defined in SAP and allows SAP to call functions defined in external applications.
3) The term Synchronous RFC refers to two-way RFC calls into or out of SAP.
4) The term Transactional RFC (tRFC) refers to one-way RFC calls into or out of SAP with guaranteed delivery.
5) The term Application Link Enabling (ALE) refers to SAP's technology for transmitting IDOC data containers to and from external applications using Transactional RFC.

Given the foregoing, it is often desirable to interface to a variety of third-party databases and information management systems. However, errors may occur in the generation, transmission and/or receipt of the data being written to or read from such third-party databases and information management systems. This typically forces the originating system to regenerate and retransmit the original data. If these tasks could be eliminated, or at least off-loaded from the originating system, a significant improvement in system performance could be had. Moreover, it is desirable to ensure that data to be written to an outside system (either from the perspective of the user's system, or that of the third-party system) is not lost in transit, if an error occurs.

SUMMARY

In one embodiment, a method for queuing data for an application server is described. The method includes creating a queue entry record corresponding to the data, storing a queue entry including the data and the corresponding queue entry record in a queue, and receiving a command regarding the data from the application server.

In another embodiment, a system for queuing data for an application server is described. The system includes a set of instructions operable to receive a command and the data from the application server, a set of instructions operable to create a queue entry record corresponding to the data, a set of instructions operable to store a queue entry including the data and the corresponding queue entry record in a queue, and a set of instructions operable to query the queue entry.

In yet another embodiment, a application server is described. The application server includes a set of instructions operable to transmit data to a queuing system for the data.

In still another embodiment, a data structure for queuing data for an application server is described. The data structure includes a file containing a data object, a queue entry record, and a reference identifier for the data object. The queue entry record includes the processing status of the data object.

The foregoing is a summary and thus contains, by necessity, simplifications, generalizations and omissions of detail; consequently, those skilled in the art will appreciate that the summary is illustrative only and is not intended to be in any way limiting. As will also be apparent to one of skill in the art, the operations disclosed herein may be implemented in a number of ways, and such changes and modifications may be made without departing from this invention and its broader aspects. Other aspects inventive features, and advantages of the present invention, as defined solely by the claims, will become apparent in the non-limiting detailed description set forth below.

BRIEF DESCRIPTION OF THE DRAWINGS

The present invention may be better understood, and its numerous objects, features, and advantages made apparent to those skilled in the art by referencing the accompanying drawings.

FIG. 1b shows an example of a computer system which can be utilized to implement the application servers shown in FIG. 1a.

The use of the same reference symbols in different drawings indicates similar or identical items.

DETAILED DESCRIPTION

Figure 1A:
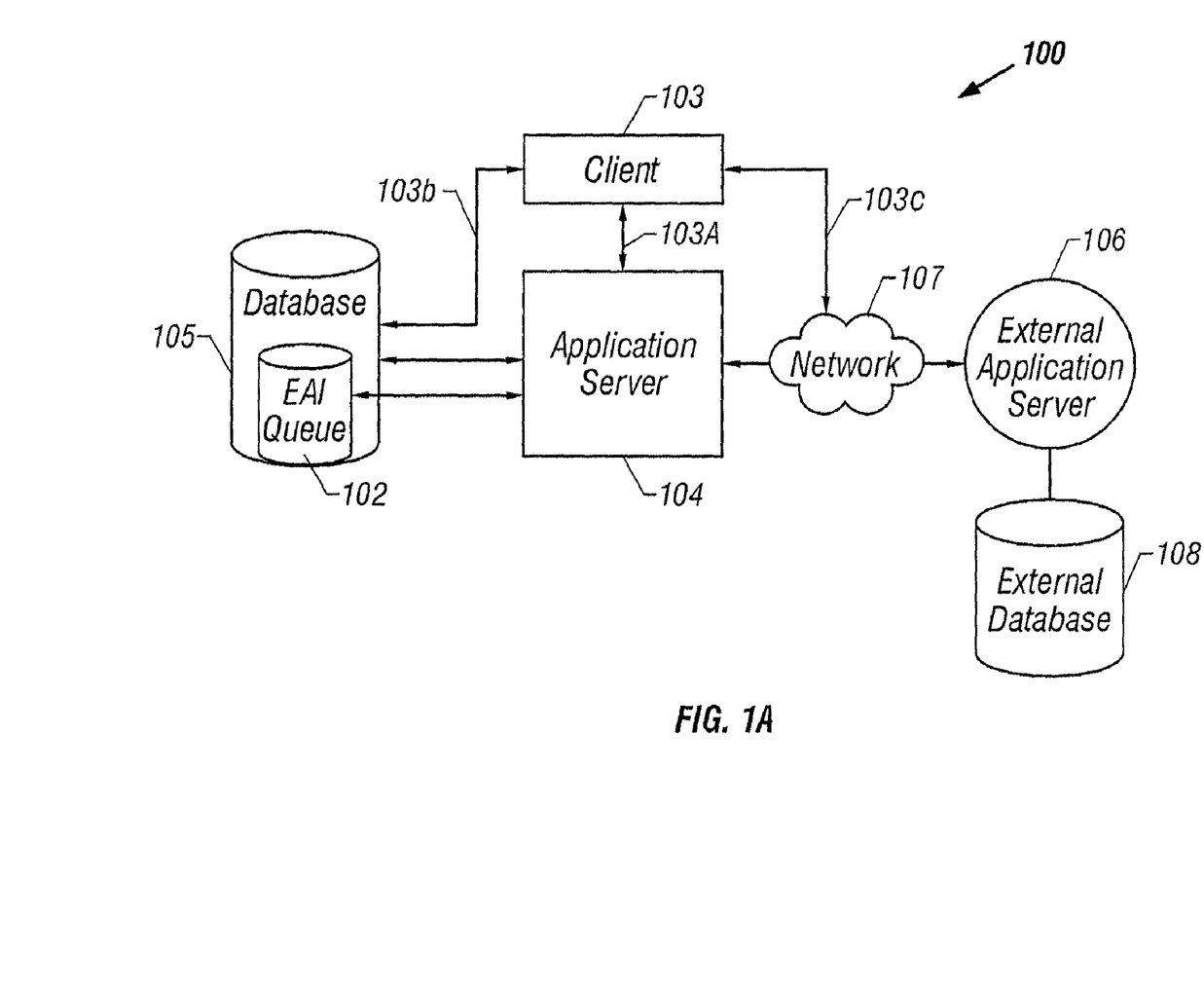
FIG. 1a shows an embodiment of a system in which an EAI queue in accordance with the present invention can be utilized.

Referring now to FIG. 1a, an embodiment of an EAI system 100 in which an EAI queue 102 in accordance with the present invention can be utilized is shown. EAI queue 102 supports transactions initiated by a client 103 by providing temporary storage for data in transit between an application server 104 (which is coupled to a database 105, of which EAT queue 102 may be a part, as depicted) and an external application server 106 (e.g., coupled to application server 104 by a communication network 107), and a means by which to monitor the data exchange. Using EAI queue 102 for temporary data storage can facilitate error recovery in the event that the flow of data to or from application server 104, external application server 106, or communication network 107 between application server 104 and external application server 106 is interrupted.

Application server 104 thus effects transactions initiated by client 103 by supporting the flow of data between database 105 and external application server 106 (via communication network 107). When such transactions are communicated between client 103 and application server 104 (depicted as communications 103a), client 103 is said to be connected. Alternatively, client 103 is capable of communicating directly with database 105 (via communications 103b) and external application server 106 (using communication network 107, via communications 103c), and so can operate in place of application server 104. In this instance, client 103 is said to be disconnected.

EAI system 100 allows front office applications on an application server 104 to be integrated with back office applications on external application server 106. For example, sales and service professionals can enter sales orders in an application program on application server 104 and receive real-time feedback on inventory availability from an external database 108. The sales or service professional can then fulfill the sales order via application server 104.

Figure 1B:
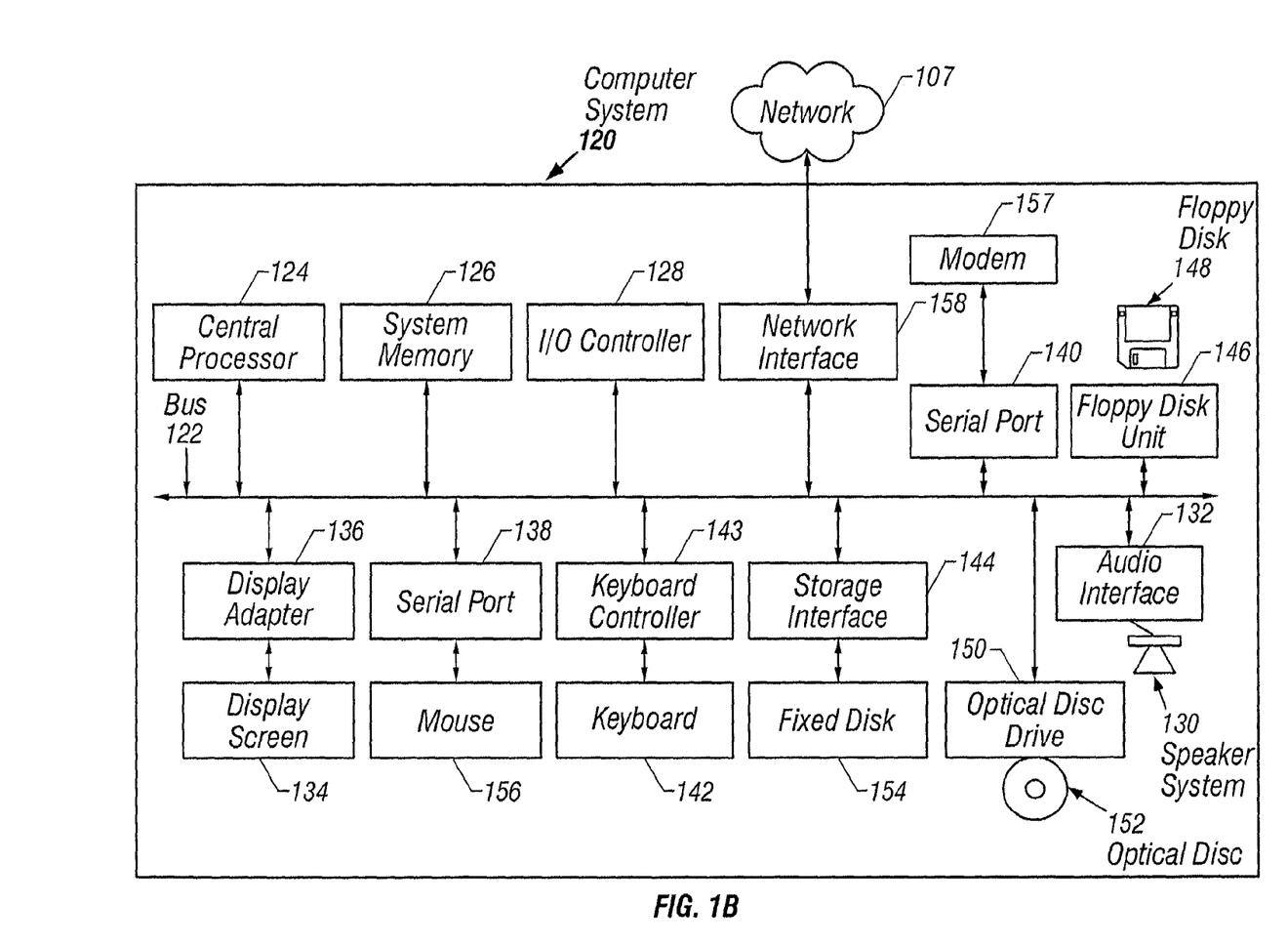

FIG. 1b depicts a block diagram of a computer system 120 suitable for implementing application server 104 and the external application server 106. Computer system 120 includes a bus 122 which interconnects major subsystems of computer system 120 such as a central processor 124, a system memory 126 (typically RAM, but which may also include ROM, flash RAM, or the like), an input/output controller 128, an external audio device such as a speaker system 130 via an audio output interface 132, an external device such as a display screen 134 via display adapter 136, serial ports 138 and 140, a keyboard 142 (interfaced with a keyboard controller 143), a storage interface 144, a floppy disk drive 146 operative to receive a floppy disk 148, and an optical disc drive 150 operative to receive an optical disc 152. Also included are a mouse 156 (or other point-and-click device, coupled to bus 122 via serial port 138), a modem 157 (coupled to bus 122 via serial port 138) and a network interface 158 (coupled directly to bus 122).

Bus 122 allows data communication between central processor 124 and system memory 126, which may include both read only memory (ROM) or flash memory (neither shown), and random access memory (RAM) (not shown), as previously noted. The RAM is generally the main memory into which the operating system and application programs are loaded and typically affords at least 16 megabytes of memory space, and preferably more. The ROM or flash memory may contain, among other code, the Basic Input-Output system (BIOS) which controls basic hardware operation such as the interaction with peripheral components. Applications resident with computer system 120 are generally stored on and accessed via a computer readable medium, such as a hard disk drive (e.g., fixed disk 154), an optical drive (e.g., CD-ROM drive 150), floppy disk unit 146 or other storage medium. Additionally, applications may be in the form of electronic signals modulated in accordance with the application and data communication technology when accessed via network modem 157 or network interface 158.

Storage interface 144, as with the other storage interfaces of computer system 120, may connect to a standard computer readable medium for storage and/or retrieval of information, such as a fixed disk drive 154. Fixed disk drive 154 may be a part of computer system 120 or may be separate and accessed through other interface systems. Many other devices can be connected such as the mouse 156 connected to bus 122 via serial port 138, a modem 157 connected to bus 122 via serial port 140 and the network interface 158 connected directly to bus 122. Modem 157 may provide a direct connection to a remote server via a telephone link or to the Internet via an internet service provider (ISP). Network interface 158 may provide a direct connection to a remote server, such as between application server 104 and the external application server 106 (FIG. 1a) via a direct network link to the Internet via a POP (point of presence). Network interface 158 may provide such connection using various communication links, such as a dial-up wired connection with a modem, a direct link such as a T1, ISDN, or cable line, a wireless connection through a cellular or satellite network, or a local data transport system such as Ethernet or token ring over a local area network.

Many other devices or subsystems (not shown) may be connected in a similar manner (e.g., bar code readers, document scanners, digital cameras and so on). Conversely, it is not necessary for all of the devices shown in FIG. 1*b* to be present to practice the present invention. The devices and subsystems may be interconnected in different ways from that shown in FIG. 1*b*. The operation of a computer system such as that shown in FIG. 1*b* is readily known in the art and is not discussed in detail in this application. Code to implement the present invention may be stored in computer-readable storage media such as one or more of system memory 126, fixed disk 154, CD-ROM 152, or floppy disk 148. Additionally, computer system 120 may be any kind of computing device, and so includes personal data assistants (PDAs), network appliance, desktop, laptop, X-window terminal or other such computing device. The operating system provided on computer system 120 may be MS-DOS®, MS-WINDOWS®, OS/2®, UNIX®, Linux® or other known operating system. Computer system 120 also supports a number of Internet access tools, including, for example, an HTTP-compliant web browser having a JavaScript interpreter, such as Netscape Navigator® 3.0, Microsoft Explorer® 3.0 and the like.

Multiple computer systems 120 can communicate with one another via network 107. One or more of the computer systems 120 can be utilized to implement the user interface module 104 (FIG. 1*a*), while one or more of the computer systems 120 can be utilized to implement server 104 (FIG. 1*a*).

Moreover, regarding the signals described herein, those skilled in the art will recognize that a signal may be directly transmitted from a first component to a second component, or a signal may be modified (e.g., amplified, attenuated, delayed, latched, buffered, inverted, filtered or otherwise modified) between the components. Although the signals of the above described embodiment are characterized as transmitted from one component to the next, other embodiments of the present invention may include modified signals in place of such directly transmitted signals as long as the informational and/or functional aspect of the signal is transmitted between components. To some extent, a signal input at a second component may be conceptualized as a second signal derived from a first signal output from a first component due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

The process of integrating an enterprise application program in EAI system 100 includes creating a business data flow to control the transformation of an external data object to an application server data object, and an application server data object to an external data object. There are two types of business data flows: Outbound to external application server 106 (Send) and Inbound from external application server 106 (Receive).

Figure 2:
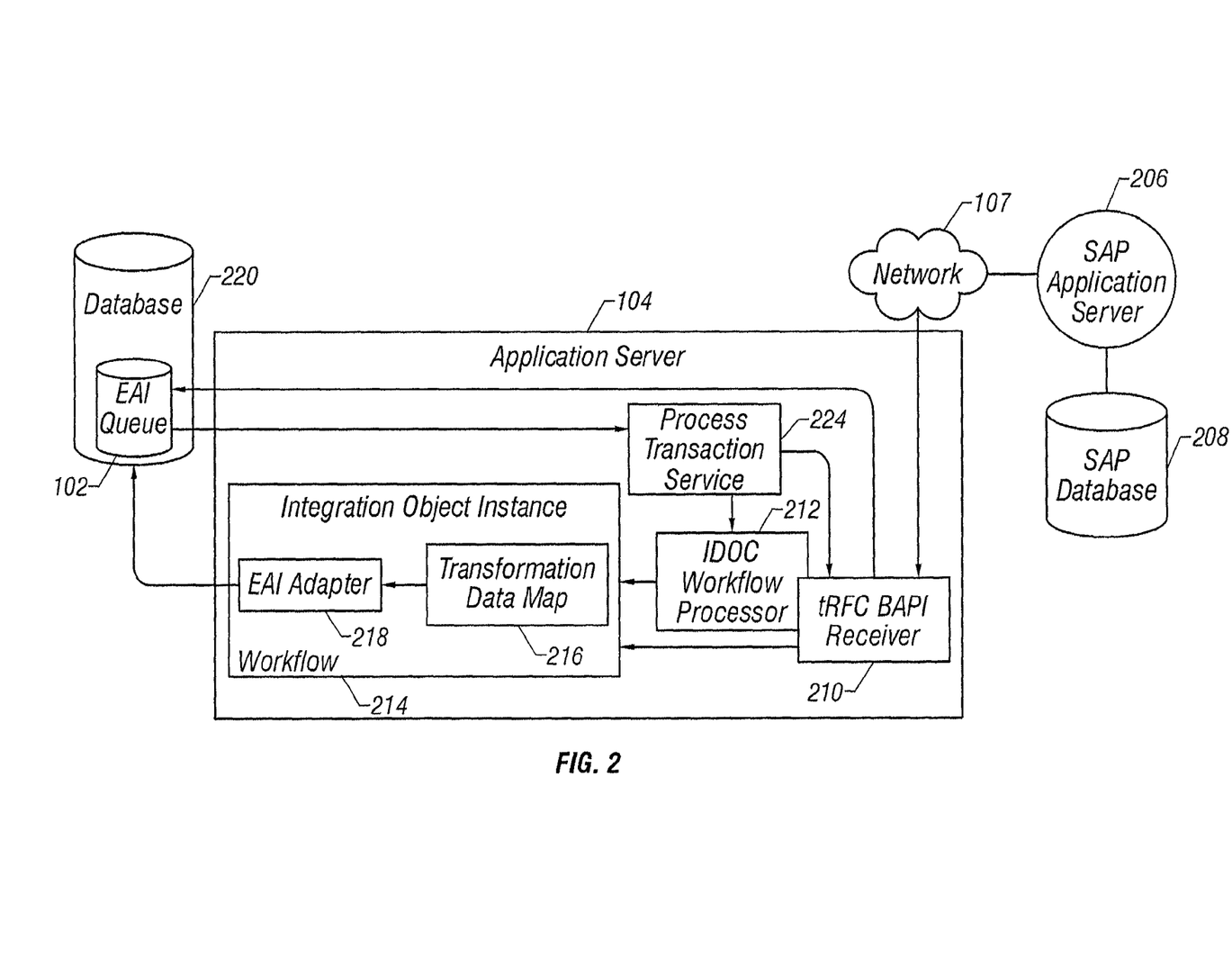
FIG. 2 shows an example of components included in an application server as shown in FIG. 1a for handling inbound business data flow.

Referring now to FIG. 2, an example of EAI queue 102 implemented with an SAP application server 206 and a SAP database 208 is shown. In one embodiment, EAI queue 102 occupies a portion of a database 220. Database 220 can be implemented using a suitable read/write storage device with read/write storage media.

Inbound business data flows start with a tRFC BAPI receiver 210. tRFC BAPI receiver 210 continuously monitors data from SAP application server 206, looking for data in IDOC or tRFC function call form. When tRFC BAPI receiver 210 receives data in the IDOC format, tRFC BAPI receiver 210 invokes an IDOC workflow processor 212 to convert the raw SAP IDOC data into an IDOC integration object. IDOC workflow processor 212 then invokes a workflow module 214 to process the data further. Workflow module 214 controls the flow and transformation of data into and out of the application programs (not shown) on application server 104.

Data from SAP application server 206 can represent either an IDOC structure in SAP or a tRFC function interface. In the embodiment shown in FIG. 2, when tRFC BAPI receiver 210 receives data from SAP application server 206 via a tRFC function interface, tRFC BAPI receiver 210 creates a BAPI integration object that it sends to workflow module 214 for processing. When tRFC BAPI receiver 210 receives data from SAP application server 206 via an IDOC structure, tRFC BAPI receiver 210 invokes IDOC workflow processor 212 to create an IDOC integration object and send it to workflow module 214 for processing.

Workflow module 214 invokes the transformation data map 216 to transform the BAPI or IDOC integration object instance into an internal integration object instance using the data mappings. The internal integration object instance is then passed to the EAI adapter 218 where it can be processed as a business object into database 220. An integration object contains meta-data that describes the structure of a data object. Integration objects can be created to describe the structure of internal business objects, SAP IDOCs, SAP BAPIs or SAP RFC calls. Workflow 214 operates on specific data instances of these integration objects.

EAI queue 102 can be used with tRFC BAPI receiver 210 to temporarily store data to ensure data recoverability should a failure occur. When the tRFC receiver 210 receives data from SAP application server 206, the data can be saved in EAI queue 102, depending upon a mode setting indicating whether data should be written to EAI queue 102 under various circumstances as described hereinbelow. A process transaction service 224 can pick up entries from EAI queue 102 and deliver them to either tRFC BAPI receiver 210 or IDOC workflow processor 212, depending on whether the data is in the IDOC format. The raw data is placed in EAI queue 102 as it was received from SAP application server 206 prior to any workflow processing.

The data transferred to application server 104 may be saved in EAI queue 102 depending upon the success or failure of workflow processing and the mode setting of tRFC BAPI receiver 210. In one embodiment, the possible mode settings are as follows:

WriteNone—EAI queue 102 is not used, and the workflow 214 is invoked. If an error occurs in workflow module 214, the error will show up in the tRFC layer in SAP application server 206.

WriteOnErr—When a call is received from SAP application server 206 and an error occurs in workflow module 214 invoked in application server 104, the data in transit is saved to EAI queue 102. If the data cannot be saved in EAI queue 102 an error is returned to the tRFC layer in SAP application server 206. If the data is saved in EAI queue 102 successfully, no error is returned to SAP application server 206 and error handling occurs in application server 104.

WriteBeforeErr—When a call is received from SAP application server 206, the data is immediately saved in EAI queue 102. Workflow module 214 is then invoked in application server 104, if it fails the data is reprocessed by the process transaction service 224 at a later time. An error is returned to the tRFC layer in SAP application server 206 only if the data cannot be saved in the queue initially. The WriteBeforeErr mode always creates an entry in EAI queue 102 regardless of error status.

WriteOnly—When a call is received from SAP application server 206, the data is immediately saved in EAI queue 102 and no immediate attempt is made to call the workflow 214. Workflow module 214 is invoked at a later time by the process transaction service 224. An error is returned to the tRFC layer in SAP application server 206 only if the data cannot be saved in EAI queue 102.

Table 1 summarizes the possible status values for a data object stored in EAI queue 102 during processing from SAP application server 206 to application server 104 in each of the above modes.

TABLE 1

| Inbound from SAP | Result of Workflow | SAP or network error | Entry in EAI Queue (status) | Transaction errors in tRFC layer |
|---|---|---|---|---|
| WRITEONLY | N/A | N/A | Yes (Initial) | No |
| WriteNone | Success | N/A | No | No |
|  | Failed | N/A | No | Yes |
| WriteOnErr | Success | N/A | No | No |
|  | Failed | N/A | Yes (Initial) | No |
| WriteBeforeErr | Success | No | Yes (Confirmed) | No |
|  | Failed | Yes | Yes (Initial or Processed) | No |

Figure 3:
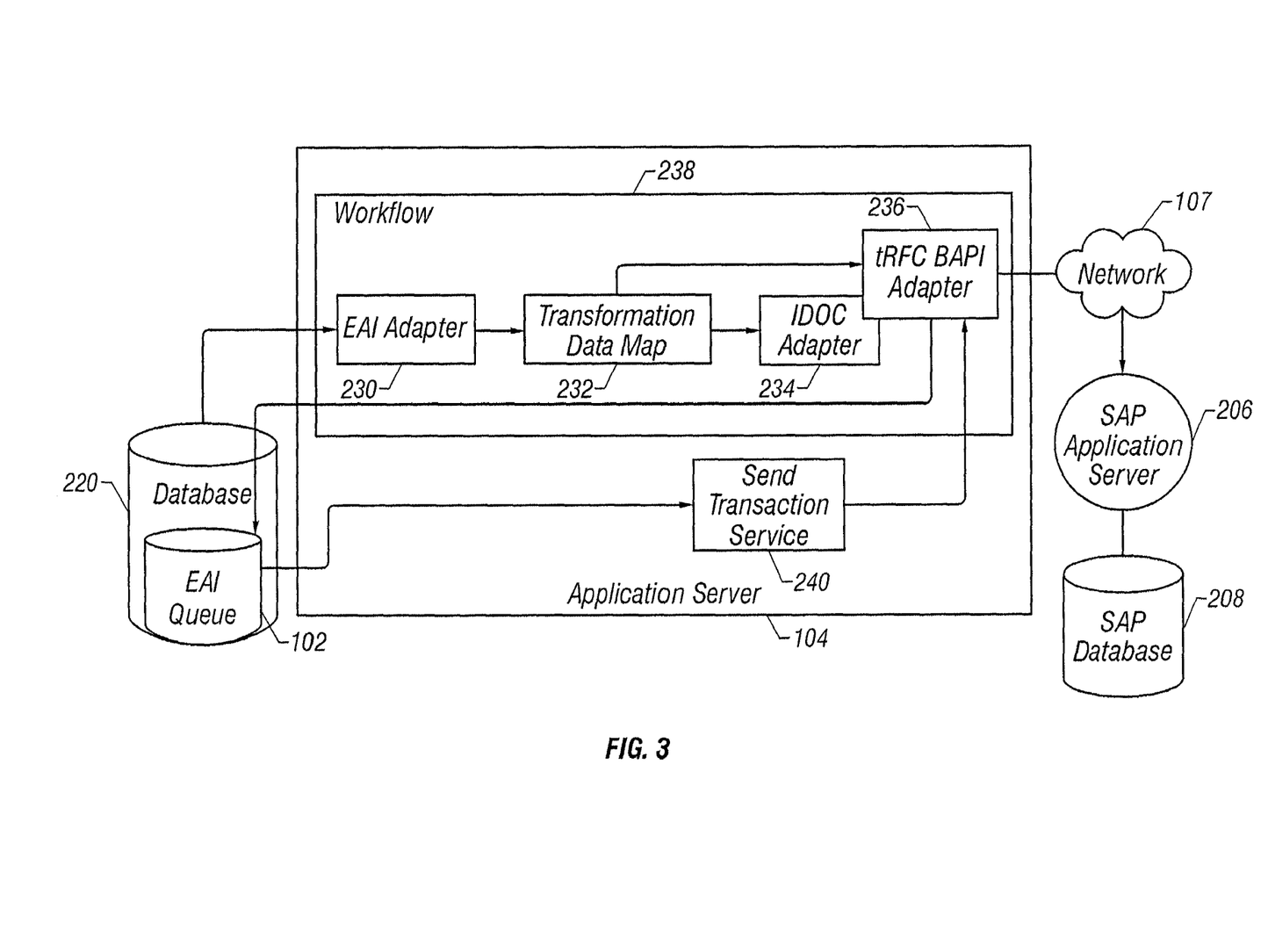
FIG. 3 shows an example of components included in an application server as shown in FIG. 1a for handling outbound business data flow.

Referring now to FIG. 3, outbound business data flows invoke an EAI Adapter 230 to extract data from database 220 that corresponds to a business object. EAI adapter 230 uses the data to populate a corresponding internal integration object instance. The integration object instance is passed to a transformation data map 232, which includes pre-configured data mappings to transform integration object instances in application server 104 to the equivalent BAPI or IDOC integration object instances. An IDOC adapter 234 converts the IDOC integration object instances into a special format and then passes that data to a BAPI adapter 236. tRFC BAPI adapter 236 interfaces to SAP application server 206 directly.

tRFC BAPI adapter 236 can be configured to save the IDOC or BAPI integration object instances resulting from workflow module 238 in EAI queue 102 until they are requested by send transaction service 238. EAI send transaction service 240 can pick up entries from EAI queue 102 and deliver them to tRFC BAPI adapter 236. tRFC BAPI adapter 236 attempts to re-send the data to SAP application server 206.

In some embodiments, tRFC BAPI adapter 236 can be configured in one of the following modes:

WriteNone—EAI queue 102 is not used. Data is sent directly to SAP application server 206.

WriteOnErr—The data in transit is saved in EAI queue 102 when network 107 or SAP application server 206 is unavailable, or an error is returned from SAP application server 206 upon a call from tRFC BAPI adapter 236. If data cannot be saved in EAI queue 102, an error is returned to the function that invoked EAI queue 102.

WriteBeforeErr—Data in transit is stored in EAI queue 102 prior to the call to SAP application server 206. If network 107 or SAP application server 206 is unavailable, or an error is returned from SAP application server 206 upon a call from tRFC BAPI adapter 236, the data has already been saved in EAI queue 102 and can be resent to SAP application server 206 by send transaction service 140. The caller receives an error only if the data cannot be saved in EAI queue 102.

WriteOnly—Data in transit is placed in EAI queue 102 and no immediate call is made to SAP application server 206 to send the data. The send transaction service 140 then sends the data at a later time. The caller receives an error only if the data cannot be saved in EAI queue 102.

Table 2 summarizes the possible status values for a data object stored in EAI queue 102 during processing from application server 104 to SAP application server 206 in each of the above modes.

TABLE 2

| Mode | Result of Workflow | Entry in EAI Queue (status) | Data passed to SAP | SAP or network error while data passed | Entry in EAI Queue (status) |
|---|---|---|---|---|---|
| WRITEONLY | Success | Yes (Initial) | No |  |  |
|  | Fail | No | No |  |  |
| WriteNone | Success | No | Yes | Yes | No |
|  | Fail | No | No | No | No |
| WriteOnErr | Success | No | Yes | Yes | Yes (Initial or Sent) |
|  | Fail | No | No | No | No |
| WriteBeforeErr | Success | Yes (Initial) | Yes | Yes | Yes Initial or Sent) |
|  | Fail | No | No | No | Yes (Confirmed) |

In one embodiment, each queue entry in EAI queue 102 can include the following information:

a file containing the data object in transit;

the processing status of the data object;

a Reference Identifier for the data object in SAP application server 206; and additional fields that can be used for error information and other information specific to SAP application server 206 or other external system.

A system administrator's console for application server 104 can present the data in EAI queue 102 and its current processing status. If errors occur while the data is in transit, an identifier for the external system and error information can be used to determine the problem, correct it, and restart the data flow between application server 104 and SAP application server 206.

Figure 4:
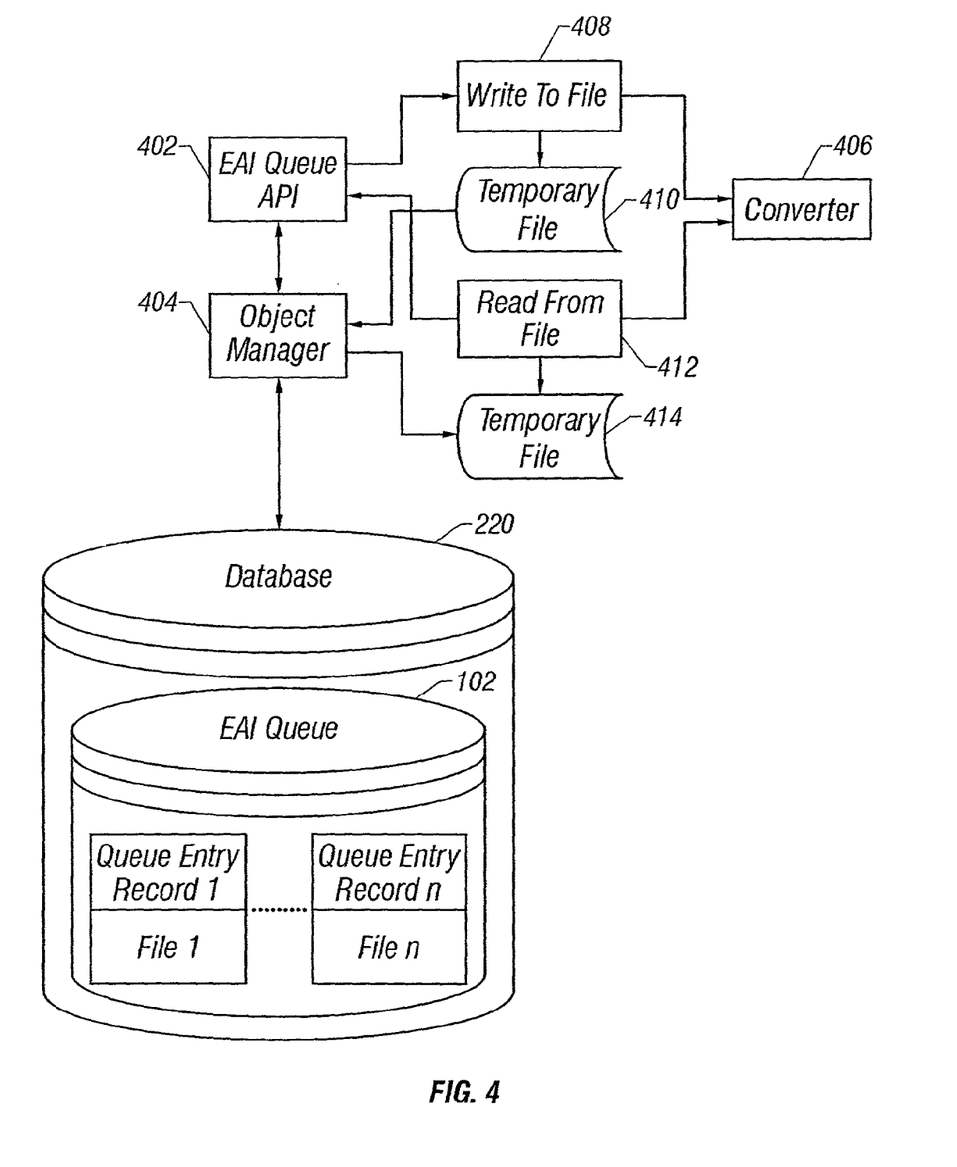
FIG. 4 shows an example of components required for processing EAI queue API methods.

Referring now to FIG. 4, an EAI queue application program interface (API) 402 is provided in the EAI system 100 (FIG. 1a) to access EAI queue 102. EAI queue API 402 includes methods to update information held in the queue and allows other components in application server 104 as well as users to develop software to use EAI queue 102. One embodiment of EAI queue API 402 includes the following methods:

AddMessage—adds a data object to EAI queue 102

GetMessage—retrieves a data object from EAI queue 102

GetStatus—retrieves processing status of the data object

UpdateStatus—updates the processing status of the data object

DeleteMessage—removes a data object from EAI queue 102

Referring to FIGS. 2 and 4, in one embodiment, status values for SAP application server 206 to application server 104 are: Initial, Processed and Confirmed. If there is an error while processing the data object in workflow module 214, the status remains as either Initial or Processed until process transaction service 224 executes. If there is an error in process transaction service 224, the status changes to "Error in Processing". By contrast, the Confirmed state indicates that no error has occurred and processing is complete. The process transaction service looks for Initial or Processed status, which imply that processing is not complete.

Referring to FIGS. 3 and 4, in one embodiment, status values from application server 104 to SAP application server 206 are: Initial, Sent, or Confirmed. If there is an error while processing the data object in workflow module 238, the status remains as either Initial or Sent until the send transaction service 140 executes. If there is an error in send transaction service 140, the status changes to "Error in Sending".

Other user properties and component parameters that affect EAI queue 102 include:
  SAPXMLQueueCleanup
  SAPXMLQueueService
  SAPXMLQueueName SAPXMLQueueCleanup defines the mode of cleanup used for entries in the queue. If the value of this is True, then entries in the queue are deleted when their status reaches Confirmed. If the value of this is False, then Confirmed entries are left in the queue and can be deleted at a later time. SAPXMLQueueName and SAPXMLQueueService allow some flexibility of configuration. SAPXMLQueueName holds the name of the queue to use, as multiple queues can be created. For instance, when IDOCs are received from SAP, they are stored in the "tRFC Inbound from SAP" queue. When IDOCs are sent to SAP, they are stored in the "tRFC Outbound to SAP" queue. SAPXMLQueueService contains the name of the EAI Queue business service used to access the queue. This is the same business service as is described herein. It is also possible for a user to create their own business service and implement the methods described herein, according to the user's needs and desires, and so override some or all of the functionality described herein. The user can change the name of the business service to point to the user's implementation.

FIG. 4 shows an example of components included in EAI queue API 402 for processing the EAI queue API methods. EAI queue API 402 is accessed through method calls from application server 104. EAI queue API 402 uses an object manager 404 to retrieve and store queue entries in database 220. It will be noted that, with regard to whether or not client 103 is connected or disconnect, the EAI queue business service can be executed either from client 103 or application server 104. When the business service is running within client 103 without an application server (e.g., application server 104), and so is disconnected, a temporary file storage mechanism is used. Alternatively, when client 103 is connected to an application server (e.g., application server 104), the business service executes within the application server and no temporary file storage mechanism is used. These alternatives are discussed below.

In the case where client 103 is disconnected (i.e., running without an application server), data is stored in the form of a file. In one embodiment, XML files are used, however, files in any suitable format can be used. The file is stored in database 220 as a file attachment to a queue entry record. Multiple queue entries (1 . . . n) can be stored in EAI queue 102. Data is passed to and from EAI queue API methods as a property set. This data is converted to the file format used in EAI queue 102 by a converter 406. For example, the data can be converted to an XML file by the converter 406. A Write to File module 408 is used to write the data to a temporary file 410 prior to storing the file as a file attachment in EAI queue 102. A Read from File module 412 reads a temporary file 414 created by the object manager 404 and converts the file back to a property set.

In the case where client 103 is connected to an application server (the normal mode of operation), no temporary files (i.e., temporary files 410 and 414) are employed, and so, there is no need to invoke write to file module 408 and read from file module 412. In this case, temporary files 410 and 414 are bypassed, with EAI queue API 402 interacting directly with converter 406. In this case, the EAI queue business service uses the converter 406 to convert the integration object to XML format (as noted above). This XML text is held in memory and passed to object manager 404. Object manager 404 then writes the XML text held in memory to a file attachment held in EAI queue 102 as part of database 220.

Figure 5:
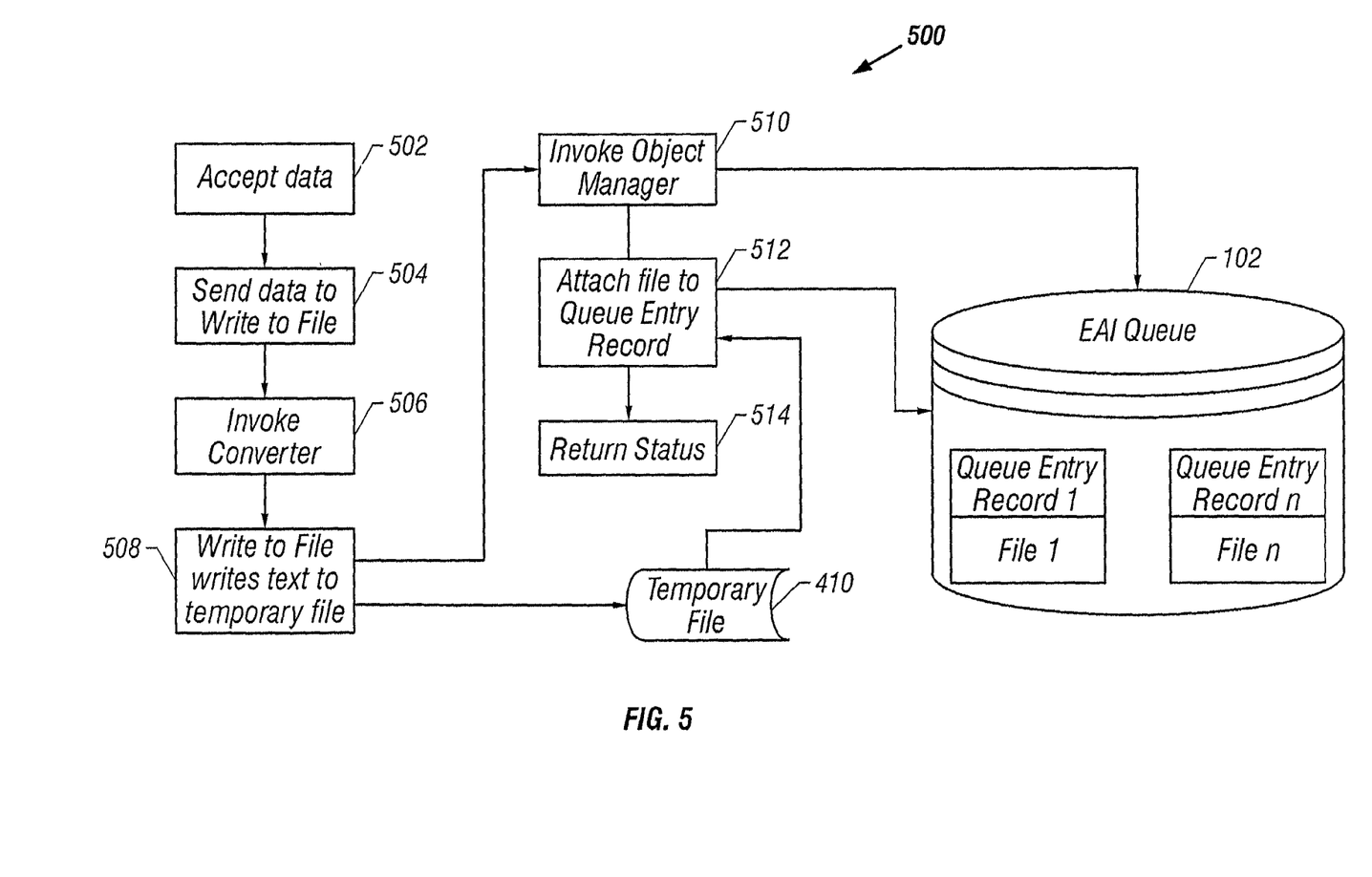
FIG. 5 shows an example of processes included in the EAI queue API AddMessage method.

Referring now to FIGS. 4 and 5, FIG. 5 shows an example of processes included in the AddMessage method 500. Process 502 accepts data in the form of a property set. As with the modules depicted in FIG. 4, the use of a temporary file depends on whether or not client 103 is used in disconnected mode.

In the case where client 103 is disconnected, process 504 passes the property set to the Write to File module 408. In process 506, the Write to File module 408 writes the property set to temporary file 410 with an appropriate format, such as an XML file. Process 510 invokes the object manager 404 to allocate space in database 220 for a new queue entry. Process 512 creates a queue entry record and attaches it to temporary file 410 to form the queue entry. The queue entry is then stored in database 220. Process 514 returns the result of the AddMessage method to client 103.

In the case where client 103 is connected to the application server (the normal mode of operation), no temporary files (i.e., temporary file 410) are employed, and so, there is no need to send data to the write to file module, nor to write text to temporary file 410. As before, temporary file 410 is bypassed. Once the data (the property set) has been accepted, converter 406 is invoked (invoke converter 506) to convert the data (property set). Once converted, the data (now in XML format) is sent to object manager 404. As before, process 510 invokes object manager 404 to allocate space in database 220 for a new queue entry. However, unlike the process described previously with regard to FIG. 4, the XML text is held in memory before being passed to object manager 404. Process 512, via object manager 404, creates a queue entry record. Object manager 404 then writes the XML text held in memory as a file attachment held in EAI queue 102 to form the queue entry. The queue entry is stored in database 220. As before, process 514 returns the result of the AddMessage method to application server 104.

TABLE 3

Table 3 shows an example of arguments that can be included to invoke the AddMessage method.

| Argument name | Input/output | Required? | Argument Type | Description |
| --- | --- | --- | --- | --- |
| Message | Input | No | Hierarchy | Input transaction data in form of the application server Message. This is written to a temporary file. |
| ReferenceID | Input | Yes | String | Reference identifier for status table |
| QueueName | Input | Yes | String | Name of queue to insert into |
| Status | Input | Yes | String | Status value for status table |
| Comments | Input | No | String | Comments for status table |

TABLE 3-continued

Table 3 shows an example of arguments that can be
included to invoke the AddMessage method.

| Argument name | Input/output | Required? | Argument Type | Description |
|---|---|---|---|---|
| RowID | Output | | String | Row identifier of new entry in queue items table. |
| SequenceID | Output | | String | Sequence identifier of new entry in queue items table. |

Figure 6:
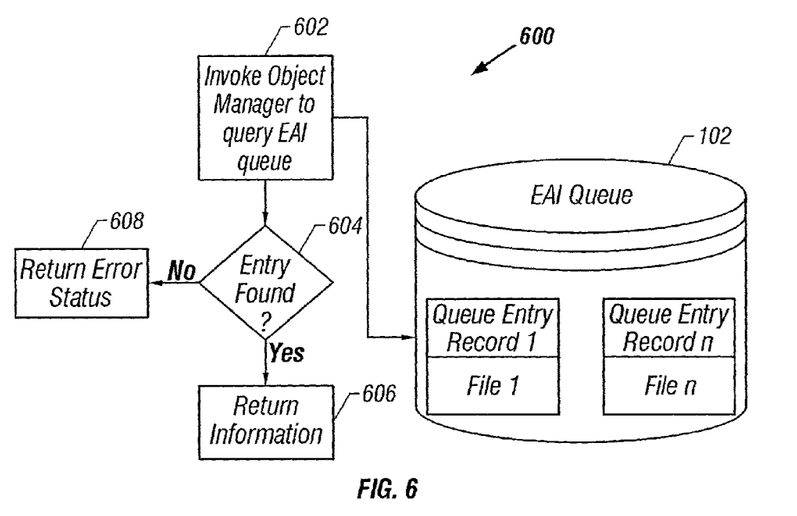
FIG. 6 shows an example of processes included in the EAI queue API GetStatus method.

Referring now to FIGS. 4 and 6, FIG. 6 shows an example of processes included in the GetStatus method 600. Process 602 invokes object manager 404 to query EAI queue 102 for queue entry information. Process 604 determines whether the queue entry being queried was found in EAI queue 102. If so, then the status of the queue entry is returned to application server 104 in process 606. Otherwise, process 608 returns an error message indicating that the queue entry being queried was not found.

TABLE 4

Table 4 shows examples of arguments that can be
included when invoking the GetStatus method.

| Argument name | Input/output | Required? | Argument Type | Description |
|---|---|---|---|---|
| RowID | Input/output | No* | String | Row ID for Queue Items Table |
| QueueName | Input | Yes | String | Type for status table |
| SearchSpec | Input | No* | Sting | Search criteria |
| SortSpec | Input | No | String | Sort criteria |
| ReferenceID | Output | | String | Reference id |
| SequenceID | Output | | String | Sequence number |
| Status | Output | | String | Status value for status table |
| Comments | Output | | String | Comments for status table |

In one embodiment of the GetStatus method, one of either RowID or SearchSpec is required. If Row ID is provided, it is the only search criteria used and that row will be retrieved. If both a SearchSpec and SortSpec are provided, the first queue entry record selected using this information is returned. If a SearchSpec is provided and no SortSpec is provided, then the queue entry records are sorted based on the sequence number and the oldest entry in EAI queue 102 that matches the SearchSpec is returned.

Figure 7:
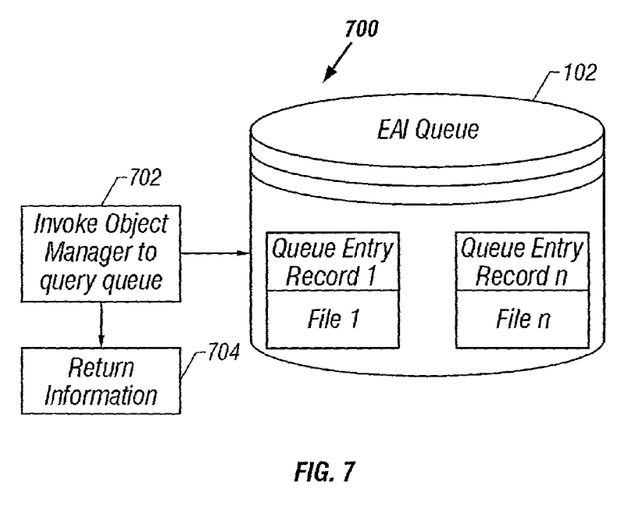
FIG. 7 shows an example of processes included in the EAI queue API UpdateStatus method.

Referring now to FIGS. 4 and 7, FIG. 7 shows an example of processes included in the UpdateStatus method 700, which updates the fields in the status record for the given RowID or SearchSpec for a queue entry record. Process 702 invokes the object manager 404 to update the status information for the specified queue entry in EAI queue 102. Process 704 returns the status information to application server 104 in process 606.

Table 5 shows examples of arguments that can be included when invoking the UpdateStatus method.

TABLE 5

| Argument name | Input/output | Required | Argument Type | Description |
|---|---|---|---|---|
| RowID | Input/Output | No* | String | Row ID of record to update |
| QueueName | Input | Yes | String | Name of queue in which to insert status |
| Status | Input | Yes | String | Status value |
| Comments | Input | No | String | Comments for status table |
| SearchSpec | Input | No* | String | Search criteria |
| SortSpec | Input | No | String | Sort criteria |
| ReferenceID | Output | | String | Reference id |
| SequenceID | Output | | String | Sequence number |
| NumberRowsAffected | Output | | String | Number of rows updated |

In one embodiment, one of either the RowID or the SearchSpec arguments is required. If the RowID is provided, it is the only search criteria used and a single row will be updated. If the SearchSpec is provided, all rows matching the search criteria are updated. If the SortSpec is provided, the first row retrieved using the SortSpec is updated, other rows are not. Reference ID and Sequence ID are output only if only one row will be returned, i.e. if RowID is input or both Sort and Search specs are provided.

Figure 8:
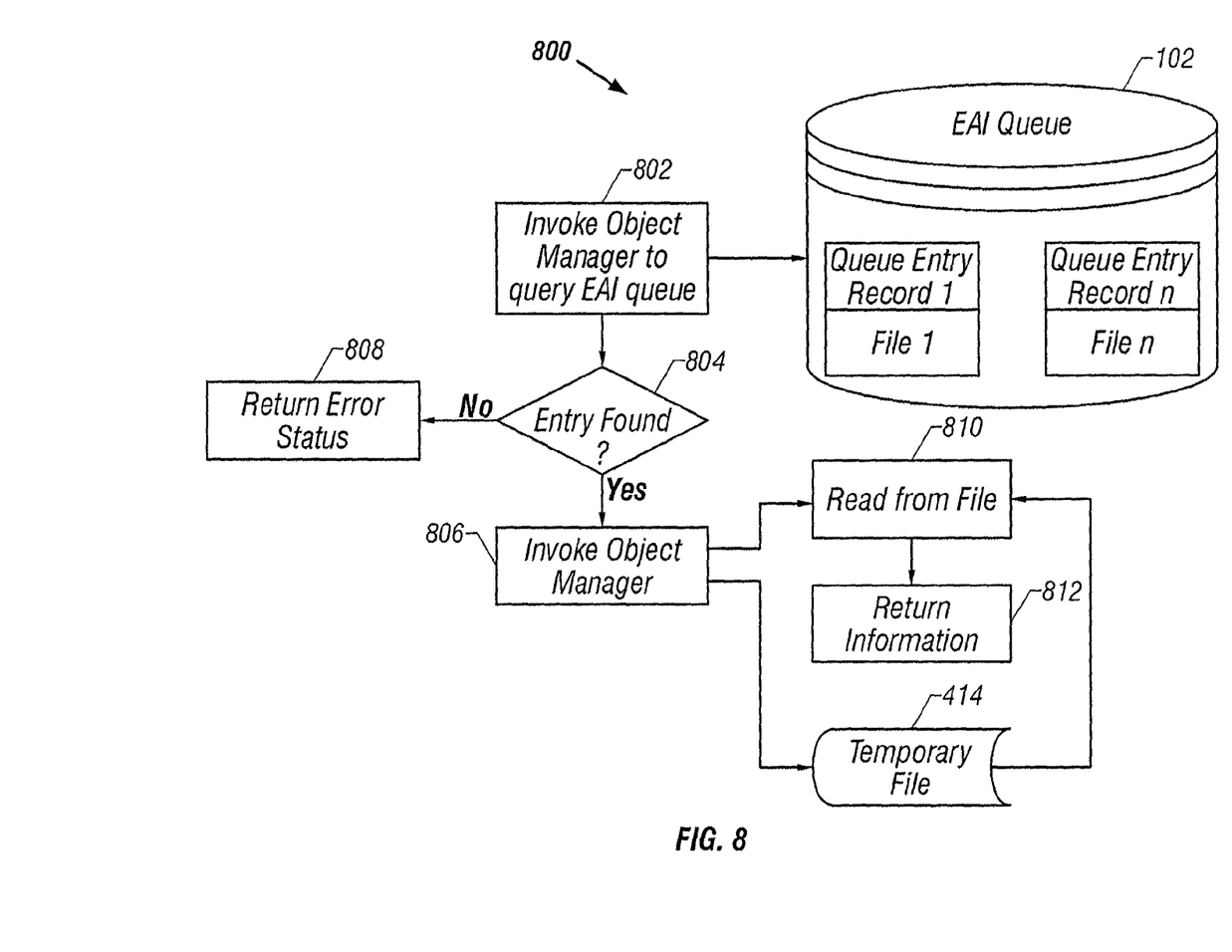
FIG. 8 shows an example of processes included in the EAI queue API GetMessage method.

Referring now to FIGS. 4 and 8, FIG. 8 shows an example of processes included in GetMessage method 800. Process 802 invokes object manager 404 to query EAI queue 102 for queue entry information. Process 804 determines whether the queue entry being queried was found in EAI queue 102. If it is determined that the queue entry sought was not found in EAI queue 102, process 808 returns an error message indicating that the queue entry being queried was not found.

If it is determined that the queue entry sought was found in EAI queue 102, one of two sets of actions is taken, depending on whether or not client 103 is disconnected. In the case where client 103 is disconnected, process 806 invokes object manager 404 to create a temporary file 414 using the file attached to the corresponding queue entry record. From process 806, process 810 invokes Read from File module 412 and converter 406 to read the text from temporary file 414 and convert that XML data into a property set. Information in the output arguments, such as shown in Table 6, and the property set are returned to client 103 in process 812.

TABLE 6

| Argument name | Input/output | Required? | Argument Type | Description |
|---|---|---|---|---|
| RowID | Input/output | No* | String | Row ID for Queue Items Table |
| QueueName | Input | Yes | String | Queue name |
| SearchSpec | Input | No* | String | Search criteria |
| SortSpec | Input | No | String | Sort criteria |
| Message | Output | | Hierarchy | Transaction data from file in the queue entry. |
| ReferenceID | Output | | String | Reference id |
| SequenceID | Output | | String | Sequence number |

TABLE 6-continued

| Argument name | Input/output | Required? | Argument Type | Description |
|---|---|---|---|---|
| Status | Output | | String | Status value for status table |
| Comments | Output | | String | Comments for status table |

In one embodiment, one of either RowID or SearchSpec is required. If Row ID is provided, it is the only search criteria used and the specified row is retrieved. If both a SearchSpec and SortSpec are provided, the first record selected using this information is returned. If a SearchSpec is provided and no SortSpec is provided, then the records are sorted based on Sequence number and the oldest entry in the queue that matches the SearchSpec is returned.

In the case where client 103 is connected to an application server (the normal mode of operation), no temporary files (i.e., temporary file 414) are employed, and so, there is no need to retrieve data using the read from file module, nor to read text from temporary file 414. Therefore, as before, temporary file 414 and process 810 (invocation of the read from file module) are bypassed. Thus, in the case where client 103 is connected, process 806 invokes object manager 404 to retrieve the file attached to the corresponding queue entry record. The XML text in the file attachment is held in memory (rather than a file) before being passed from object manager 404. Once object manager 404 is invoked and retrieves the requisite data, converter 406 is invoked by process 810. Object manager 404 passes the XML data to converter 406, in order to convert the XML data into a property set. Information in the output arguments, such as shown in Table 6, and the property set are returned to application server 104 by process 812.

Figure 9:
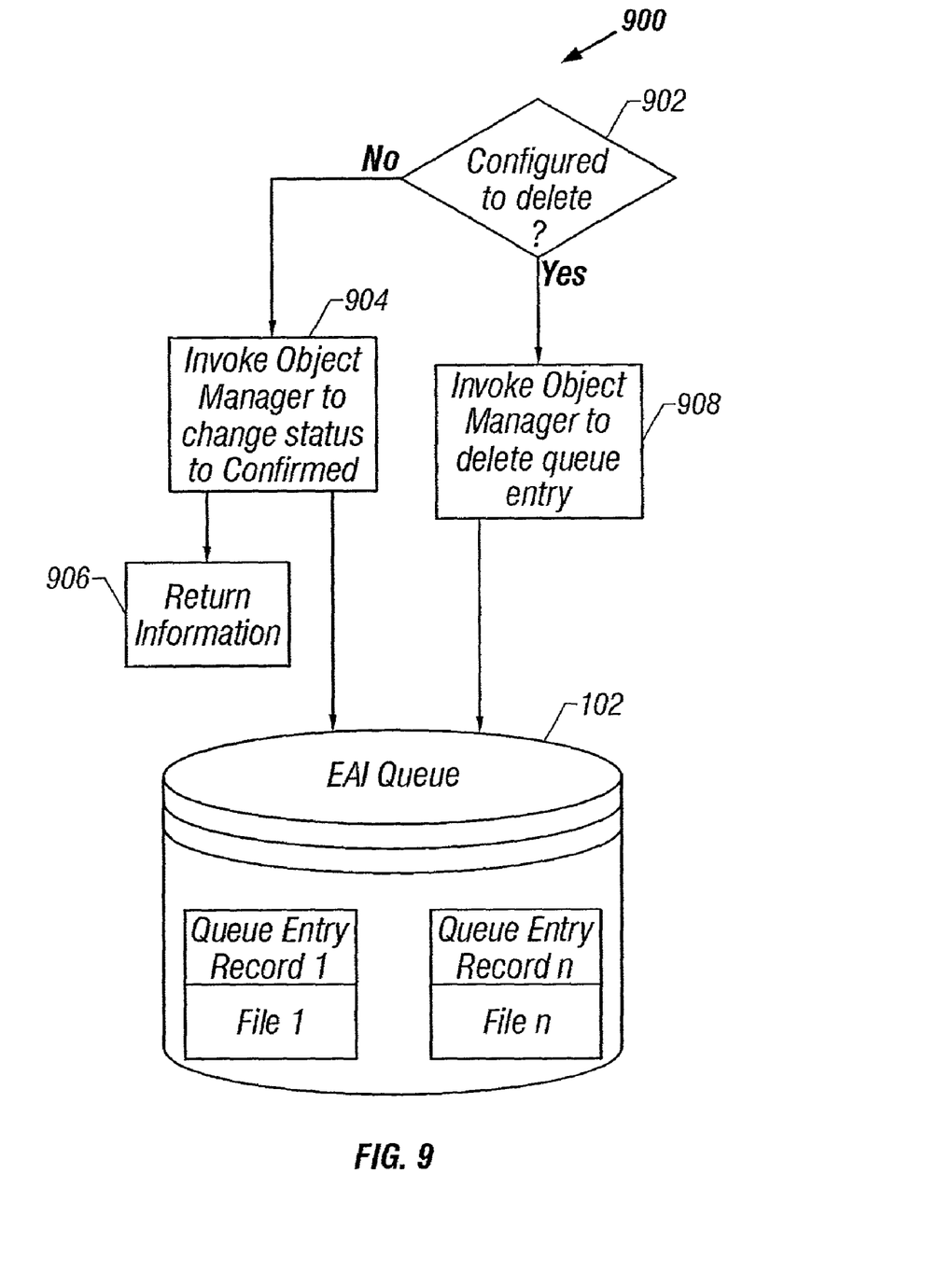
FIG. 9 shows an example of processes included in the EAI queue API DeleteMessage method.

Referring now to FIGS. 4 and 9, FIG. 9 shows an example of processes included in DeleteMessage method 900, which either deletes the status record of a queue entry or updates its status to "Confirmed". Process 902 determines whether the specified queue entry(s) are to be deleted based on the value of a DeleteStatusRecord argument. If the DeleteStatusRecord argument is "False," process 904 invokes the object manager 404 to change the status of the queue entry to "Confirmed", indicating that the queue entry was found in EAI queue 102. Process 906 returns the "Confirmed" status of the queue entry.

Referring again to process 902, if the DeleteStatusRecord argument is "True," process 908 invokes object manager 404 to delete the specified queue entry, including the queue entry record and the file attachment.

Table 7 shows examples of arguments that can be included when invoking the DeleteMessage method. In one embodiment, one of either RowID or SearchSpec arguments is required. If Row ID is provided, it is the only search criteria used and a single row will be deleted. If a SearchSpec is provided, all rows matching the search criteria are deleted. If a SortSpec is provided, the first row retrieved using the SortSpec is deleted, other rows are not.

TABLE 7

| Argument name | Input/output | Required? | Argument Type | Description |
|---|---|---|---|---|
| RowID | Input | No* | String | Row ID for Queue Items Table |
| DeleteStatusRecord | Input | No | String | Value of 'True' or 'False', False is default |
| QueueName | Input | Yes | String | Type for status table |
| Status | Input | No | String | Status value for status table - used if not deleting status record |
| Comments | Input | No | String | Comments for status table - used if not deleting status record |
| SearchSpec | Input | No* | String | Search criteria |
| SortSpec | Input | No | String | Sort criteria |
| NumberRowsAffected | Output | | String | Number of rows deleted/updated |

The foregoing detailed description has set forth various embodiments of the present invention via the use of block diagrams, flowcharts, and examples. It will be understood by those within the art that each block diagram component, flowchart step, and operations and/or components illustrated by the use of examples can be implemented, individually and/or collectively, by a wide range of hardware, software, firmware, or any combination thereof.

The present invention has been described in the context of a fully functional computer system, however those skilled in the art will appreciate that the present invention is capable of being distributed as a program product in a variety of forms, and that the present invention applies equally regardless of the particular type of signal bearing media used to actually carry out the distribution. Examples of signal bearing media include: recordable type media such as floppy disks and CD-ROM, transmission type media such as digital and analog communications links, as well as media storage and distribution systems developed in the future.

The above description is intended to be illustrative of the invention and should not be taken to be limiting. Other embodiments within the scope of the present invention are possible. Those skilled in the art will readily implement the steps necessary to provide the structures and the methods disclosed herein, and will understand that the process parameters and sequence of steps are given by way of example only and can be varied to achieve the desired structure as well as modifications that are within the scope of the invention. Variations and modifications of the embodiments disclosed herein can be made based on the description set forth herein, without departing from the spirit and scope of the invention as set forth in the following claims.

We claim:

1. A computer program product comprising:
a non-transitory computer readable medium; and
computer-executable instructions encoded on the non-transitory computer readable medium and configured to perform acts comprising:
receiving a command and data object from an external application server;
converting the data object, wherein
the data object is received in a received format,
the received format is compatible with the external application server, the converting converts the data object from the
received format into a queue format,
the queue format is compatible with a queue,
the queue format comprises identifying information,
the identifying information is configured to identify
the data object and application-specific information, and
the application-specific information is specific to the
external application server;
creating a queue entry record corresponding to the data
object;
determining whether a queue entry can be stored in the
queue, wherein
the queue entry comprises the data object and the corresponding queue entry record;
if the queue entry can be stored in the queue, storing the
queue entry in the queue;
attempting to locate the queue entry in the queue, using
the identifying information; and
if the queue entry is located in the queue,
querying the queue,
processing the data object from the queue entry,
wherein the processing comprises
converting the data object from the queue format
into the received format,
converting the data object in the received format
into an integration object, and
transforming the integration object into an internal
integration object, wherein
the transforming uses a transformation data map, and
the integration object is recognizable by the application server.

2. The non-transitory computer readable medium of claim 1, wherein the queue entry further comprises a status record, and the computer-executable instructions are further configured to update the status record.

3. The non-transitory computer readable medium of claim 1, wherein the queue entry further comprises a status record, and the instructions are further configured to retrieve a status value in the status record and return the status value to the external application server.

4. The non-transitory computer readable medium of claim 1, wherein the computer-executable instructions are further configured to transmit the data object from the queue entry to the external application server.

5. The non-transitory computer readable medium of claim 1, wherein the computer-executable instructions are further configured to convert the data object to a file before storing the queue entry.

6. The non-transitory computer readable medium of claim 5, wherein the computer-executable instructions are further configured to retrieve the file from the queue entry and to convert the file to a property set.

7. The non-transitory computer readable medium of claim 1, wherein the computer-executable instructions are further configured to:
return an error regarding the data object to the external
application server, if the queue entry cannot be stored in
the queue.

8. The non-transitory computer readable medium of claim 1, wherein the computer-executable instructions are further configured to:
delete the queue entry from the queue, if the processing is
successful; and
recover the data object from the queue entry, if the processing fails.

9. The non-transitory computer readable medium of claim 1, wherein the computer-executable instructions are further configured to:
return an error regarding the queue entry, if the queue entry
cannot be located in the queue.

10. A method comprising:
receiving a command and data object from an external
application server;
converting the data object, wherein
the data object is received in a received format,
the received format is compatible with the external
application server,
the converting converts the data object from the received
format into a queue format,
the queue format is compatible with a queue,
the queue format comprises identifying information,
the identifying information is configured to identify the
data object and application-specific information, and
the application-specific information is specific to the
external application server;
creating a queue entry record corresponding to the data
object;
determining whether a queue entry can be stored in the
queue, wherein
the queue entry comprises the data object and the corresponding queue entry record;
if the queue entry can be stored in the queue, storing the
queue entry in the queue;
attempting to locate the queue entry in the queue using the
identifying information; and
if the queue entry is located in the queue,
querying the queue entry,
processing the data object from the queue entry, wherein
the processing comprises
converting the data object from the queue format
into the received format,
converting the data object in the received format
into an integration object, and
transforming the integration object into an internal
integration object, wherein
the transforming uses a transformation data map, and
the integration object is recognizable by the application server.

11. The method of claim 10, wherein the queue entry further comprises a status record, the method further comprising:
updating the status record.

12. The method of claim 10, wherein the queue entry further comprises a status record, the method further comprising:
retrieving a status value in the status record; and
returning the status value to the external application server.

13. The method of claim 10, further comprising:
retrieving the data object from the queue entry; and
transmitting the data object to the external application
server.

14. The method of claim 10, wherein
the converting converts the data object to a file before
storing the queue entry.

15. The method of claim 14, further comprising:
retrieving the file from the queue entry; and
converting the file to a property set.

16. The method of claim 10, further comprising:
returning an error regarding the data object to the external
application server, if the queue entry cannot be stored in
the queue.

17. The method of claim 10, further comprising:
deleting the queue entry from the queue, if the processing is successful; and
recovering the data object from the queue entry, if the processing fails.

18. The method of claim 10, further comprising:
returning an error regarding the queue entry, if the queue entry cannot be located in the queue.

19. A system comprising:
a processor; and
memory, coupled to the processor, wherein the memory stores program instructions executable by the processor to:
receive a command and data object from an external application server, wherein
the data object is received in a received format, and
the received format is compatible with the external application server;
convert the data object from the received format into a queue format, wherein
the queue format is compatible with a queue,
the queue format comprises identifying information,
the identifying information is configured to identify the data object and application-specific information, and
the application-specific information is specific to the external application server;
create a queue entry record corresponding to the data object;
determine whether a queue entry can be stored in a queue, wherein
the queue entry comprises the data object and the corresponding queue entry record;
store the queue entry, if the queue entry can be stored in the queue;
attempt to locate the queue entry in the queue using the identifying information;
query the queue entry, if the queue entry is located in the queue; and
process the data object from the queue entry, if the queue entry can be located in the queue, wherein
the program instructions are further executable to
convert the data object from the queue format into the received format,
convert the data object in the received format into an integration object, and
transform the integration object into an internal integration, object using a transformation data map, wherein the integration object is recognizable by the application server.

20. The system of claim 19, wherein the queue entry further comprises a status record and the program instructions are further executable to update the status record.

21. The system of claim 19, wherein the queue entry further comprises a status record and the program instructions are further executable to retrieve a status value in the status record; and return the status value to the external application server.

22. The system of claim 19, wherein the program instructions are further executable to:
retrieve the data object from the queue entry; and
transmit the data object to the external application server.

23. The system of claim 19, wherein the program instructions are further executable to:
convert the data object to a file before storing the queue entry.

24. The system of claim 23, wherein the program instructions are further executable to:
retrieve the file from the queue entry; and
convert the file to a property set.

25. The system of claim 19, wherein the program instructions are further executable to:
return an error regarding the data object to the external application server, if the queue entry cannot be stored in the queue.

26. The system of claim 19, wherein the program instructions are further executable to:
delete the queue entry from the queue, if the processing is successful; and
recover the data object from the queue entry, if the processing fails.

27. The system of claim 19, wherein the program instructions are further executable to:
return an error regarding the queue entry, if the queue entry cannot be located in the queue.

* * * * *

UNITED STATES PATENT AND TRADEMARK OFFICE
CERTIFICATE OF CORRECTION

| | | |
|---|---|---|
| PATENT NO. | : 7,953,788 B2 | Page 1 of 1 |
| APPLICATION NO. | : 09/968134 | |
| DATED | : May 31, 2011 | |
| INVENTOR(S) | : Freese et al. | |

It is certified that error appears in the above-identified patent and that said Letters Patent is hereby corrected as shown below:

In column 3, line 46, delete "EAT" and insert -- EAI --, therefor.

In column 6, line 28, delete "RFC" and insert -- tRFC --, therefor.

In column 15, line 40, in Claim 3, after "the" insert -- computer-executable --.

In column 18, line 3-4, in Claim 19, delete "integration," and insert -- integration --, therefor.

Signed and Sealed this
Twenty-fifth Day of October, 2011

David J. Kappos
*Director of the United States Patent and Trademark Office*